US008386276B1

(12) United States Patent
Liu et al.

(10) Patent No.: US 8,386,276 B1
(45) Date of Patent: Feb. 26, 2013

(54) SYSTEMS AND METHODS FOR DETERMINING PRESCRIBING PHYSICIAN ACTIVITY LEVELS

(75) Inventors: David Liu, Atlanta, GA (US); Sean Daniel Reisz, Tucker, GA (US); Thomas A. Picard, Suwanee, GA (US)

(73) Assignee: McKesson Financial Holdings Limited (BM)

( * ) Notice: Subject to any disclaimer, the term of this patent is extended or adjusted under 35 U.S.C. 154(b) by 309 days.

(21) Appl. No.: 12/704,209

(22) Filed: Feb. 11, 2010

(51) Int. Cl.
G06Q 10/00 (2006.01)
G06Q 50/00 (2012.01)
(52) U.S. Cl. .............................. 705/2; 705/3; 707/999.1
(58) Field of Classification Search .................... 221/13; 235/85; 707/999.1
See application file for complete search history.

(56) References Cited

U.S. PATENT DOCUMENTS

| | | | |
|---|---|---|---|
| 4,674,041 A | 6/1987 | Lemon et al. |
| 4,723,212 A | 2/1988 | Mindrum et al. |
| 4,910,672 A | 3/1990 | Off et al. |
| 5,007,641 A | 4/1991 | Seidman |
| 5,080,364 A | 1/1992 | Seidman |
| 5,173,851 A | 12/1992 | Off et al. |
| 5,201,010 A | 4/1993 | Deaton et al. |
| 5,235,702 A | 8/1993 | Miller |
| 5,237,620 A | 8/1993 | Deaton et al. |
| 5,301,105 A | 4/1994 | Cummings |
| 5,305,196 A | 4/1994 | Deaton et al. |
| 5,327,508 A | 7/1994 | Deaton et al. |
| 5,359,509 A | 10/1994 | Little et al. |
| 5,388,165 A | 2/1995 | Deaton et al. |
| 5,430,644 A | 7/1995 | Deaton et al. |
| 5,448,471 A | 9/1995 | Deaton et al. |
| 5,544,044 A | 8/1996 | Leatherman |
| 5,550,734 A | 8/1996 | Tarter et al. |
| 5,588,649 A | 12/1996 | Blumberg et al. |
| 5,592,560 A | 1/1997 | Deaton et al. |
| 5,612,868 A | 3/1997 | Off et al. |
| 5,621,812 A | 4/1997 | Deaton et al. |
| 5,628,530 A | 5/1997 | Thornton |
| 5,638,457 A | 6/1997 | Deaton et al. |
| 5,642,485 A | 6/1997 | Deaton et al. |

(Continued)

FOREIGN PATENT DOCUMENTS

| | | |
|---|---|---|
| CA | 2482370 A1 | 3/2006 |
| EP | 1310895 A2 | 11/2002 |

(Continued)

OTHER PUBLICATIONS

Sampson, R.J., Taking Control of Health Care Costs, Best's Review—Life Health Insurance Edition, Nov. 1983, pp. 64-66, vol. 84, Issue 7, USA.

(Continued)

*Primary Examiner* — Michelle Le
(74) *Attorney, Agent, or Firm* — Sutherland Asbill & Brennan LLP

(57) ABSTRACT

Systems and methods may determine prescribing physician activity levels. Information associated with a plurality of healthcare transaction requests that are received during a designated time period from at least one healthcare provider computer for communication to one or more claims processor computers may be collected. A respective prescribing physician for each of the plurality of received healthcare transaction requests may be identified. For each identified physician, a respective activity measure for the designated time period may be calculated based upon a respective number of the healthcare transaction requests identifying the physician.

16 Claims, 5 Drawing Sheets

U.S. PATENT DOCUMENTS

| | | |
|---|---|---|
| 5,644,723 A | 7/1997 | Deaton et al. |
| 5,644,778 A | 7/1997 | Burks et al. |
| 5,649,114 A | 7/1997 | Deaton et al. |
| 5,659,469 A | 8/1997 | Deaton et al. |
| 5,675,662 A | 10/1997 | Deaton et al. |
| 5,687,322 A | 11/1997 | Deaton et al. |
| 5,704,044 A | 12/1997 | Tarter et al. |
| 5,748,907 A | 5/1998 | Crane |
| 5,749,907 A | 5/1998 | Mann |
| 5,832,447 A | 11/1998 | Rieker et al. |
| 5,832,457 A | 11/1998 | O'Brien |
| 5,845,255 A | 12/1998 | Mayaud |
| 5,857,175 A | 1/1999 | Day et al. |
| 5,892,827 A | 4/1999 | Beach et al. |
| 5,892,900 A | 4/1999 | Ginter et al. |
| 5,915,007 A | 6/1999 | Klapka |
| 5,926,795 A | 7/1999 | Williams |
| 5,950,169 A | 9/1999 | Borghesi et al. |
| 5,956,736 A | 9/1999 | Hanson et al. |
| 5,963,915 A | 10/1999 | Kirsch |
| 5,970,469 A | 10/1999 | Scroggie et al. |
| 5,974,399 A | 10/1999 | Giuliani et al. |
| 5,991,750 A | 11/1999 | Watson |
| 6,006,242 A | 12/1999 | Poole et al. |
| 6,012,035 A | 1/2000 | Freeman, Jr. et al. |
| 6,014,634 A | 1/2000 | Scroggie et al. |
| 6,021,392 A | 2/2000 | Lester et al. |
| 6,026,370 A | 2/2000 | Jermyn |
| 6,041,309 A | 3/2000 | Laor |
| 6,055,573 A | 4/2000 | Gardenswartz et al. |
| 6,067,069 A | 5/2000 | Krause |
| 6,067,524 A | 5/2000 | Byerly et al. |
| 6,073,104 A | 6/2000 | Field |
| 6,185,541 B1 | 2/2001 | Scroggie et al. |
| 6,195,612 B1 | 2/2001 | Pack-Harris |
| 6,202,923 B1 | 3/2001 | Boyer et al. |
| 6,205,455 B1 | 3/2001 | Umen |
| 6,208,973 B1 | 3/2001 | Boyer et al. |
| 6,224,387 B1 | 5/2001 | Jones |
| 6,240,394 B1 | 5/2001 | Uecker |
| 6,260,758 B1 | 7/2001 | Blumberg |
| 6,278,979 B1 | 8/2001 | Williams |
| 6,282,516 B1 | 8/2001 | Giuliani |
| 6,298,330 B1 | 10/2001 | Gardenswartz et al. |
| 6,304,849 B1 | 10/2001 | Uecker et al. |
| 6,307,940 B1 | 10/2001 | Yamamoto et al. |
| 6,307,958 B1 | 10/2001 | Deaton et al. |
| 6,321,210 B1 | 11/2001 | O'Brien et al. |
| 6,324,516 B1 | 11/2001 | Shults et al. |
| 6,330,546 B1 | 12/2001 | Gopinathan et al. |
| 6,334,108 B1 | 12/2001 | Deaton et al. |
| 6,341,265 B1 | 1/2002 | Provost et al. |
| 6,343,271 B1 | 1/2002 | Peterson et al. |
| 6,351,735 B1 | 2/2002 | Deaton et al. |
| 6,377,935 B1 | 4/2002 | Deaton et al. |
| 6,424,949 B1 | 7/2002 | Deaton et al. |
| 6,427,020 B1 | 7/2002 | Rhoads |
| 6,484,146 B2 | 11/2002 | Day et al. |
| 6,584,448 B1 | 6/2003 | Laor |
| 6,632,251 B1 | 10/2003 | Rutten et al. |
| 6,671,692 B1 | 12/2003 | Marpe et al. |
| 6,671,693 B1 | 12/2003 | Marpe et al. |
| 6,684,195 B1 | 1/2004 | Deaton et al. |
| 6,714,918 B2 | 3/2004 | Hillmer et al. |
| 6,757,898 B1 | 6/2004 | Ilsen et al. |
| 6,769,228 B1 | 8/2004 | Mahar |
| 6,795,809 B2 | 9/2004 | O'Brien et al. |
| 6,879,959 B1 | 4/2005 | Chapman et al. |
| 6,885,994 B1 | 4/2005 | Scroggie et al. |
| 7,013,284 B2 | 3/2006 | Guyan et al. |
| 7,024,374 B1 | 4/2006 | Day et al. |
| 7,058,584 B2 | 6/2006 | Kosinski et al. |
| 7,058,591 B2 | 6/2006 | Giuliani et al. |
| 7,111,173 B1 | 9/2006 | Scheidt |
| 7,155,397 B2 | 12/2006 | Alexander et al. |
| 7,225,052 B2 | 5/2007 | Foote et al. |
| 7,228,285 B2 | 6/2007 | Hull et al. |
| 7,233,913 B2 | 6/2007 | Scroggie et al. |
| 7,309,001 B2 | 12/2007 | Banfield et al. |
| 7,356,460 B1 | 4/2008 | Kennedy et al. |
| 7,380,707 B1 | 6/2008 | Fredman |
| 7,401,027 B2 | 7/2008 | Moore et al. |
| 7,415,426 B2 | 8/2008 | Williams et al. |
| 7,418,400 B1 | 8/2008 | Lorenz |
| 7,426,480 B2 | 9/2008 | Granger et al. |
| 2001/0001014 A1 | 5/2001 | Akins, III et al. |
| 2001/0032099 A1 | 10/2001 | Joao |
| 2001/0037216 A1 | 11/2001 | Oscar et al. |
| 2001/0037224 A1 | 11/2001 | Eldridge et al. |
| 2001/0041993 A1 | 11/2001 | Campbell |
| 2002/0002495 A1 | 1/2002 | Ullman |
| 2002/0035488 A1 | 3/2002 | Aquila et al. |
| 2002/0044043 A1 | 4/2002 | Chaco et al. |
| 2002/0049617 A1 | 4/2002 | Lencki et al. |
| 2002/0055856 A1 | 5/2002 | Adams |
| 2002/0065687 A1 | 5/2002 | Onoue |
| 2002/0087554 A1 | 7/2002 | Seelinger |
| 2002/0087583 A1 | 7/2002 | Morgan et al. |
| 2002/0111832 A1 | 8/2002 | Judge |
| 2002/0120473 A1 | 8/2002 | Wiggins |
| 2002/0128883 A1 | 9/2002 | Harris |
| 2002/0133503 A1 | 9/2002 | Amar et al. |
| 2002/0138593 A1 | 9/2002 | Novak et al. |
| 2002/0175370 A1 | 11/2002 | Bockelman |
| 2002/0183979 A1 | 12/2002 | Wildman |
| 2002/0198831 A1 | 12/2002 | Patricelli et al. |
| 2003/0009357 A1 | 1/2003 | Pish |
| 2003/0009367 A1 | 1/2003 | Morrison |
| 2003/0028404 A1 | 2/2003 | Herron et al. |
| 2003/0050799 A1 | 3/2003 | Jay et al. |
| 2003/0069760 A1 | 4/2003 | Gelber |
| 2003/0074218 A1 | 4/2003 | Liff et al. |
| 2003/0074222 A1 | 4/2003 | Rosow et al. |
| 2003/0083903 A1 | 5/2003 | Myers |
| 2003/0120588 A1 | 6/2003 | Dodd et al. |
| 2003/0125986 A1 | 7/2003 | Collosi |
| 2003/0149594 A1 | 8/2003 | Beazley et al. |
| 2003/0149625 A1 | 8/2003 | Leonardi et al. |
| 2003/0154163 A1 | 8/2003 | Phillips et al. |
| 2003/0229540 A1 | 12/2003 | Algiene |
| 2004/0006490 A1 | 1/2004 | Gingrich et al. |
| 2004/0019464 A1 | 1/2004 | Martucci et al. |
| 2004/0039599 A1 | 2/2004 | Fralic |
| 2004/0046020 A1 | 3/2004 | Andreasson et al. |
| 2004/0049422 A1 | 3/2004 | Mortimer |
| 2004/0054657 A1 | 3/2004 | Takeyama |
| 2004/0073457 A1 | 4/2004 | Kalies |
| 2004/0074457 A1 | 4/2004 | Maas et al. |
| 2004/0078234 A1 | 4/2004 | Tallal, Jr. et al. |
| 2004/0093242 A1 | 5/2004 | Cadigan et al. |
| 2004/0107117 A1 | 6/2004 | Denny |
| 2004/0111277 A1 | 6/2004 | Pearson et al. |
| 2004/0111291 A1 | 6/2004 | Dust et al. |
| 2004/0117323 A1 | 6/2004 | Mindala |
| 2004/0148198 A1 | 7/2004 | Kalies |
| 2004/0153336 A1 | 8/2004 | Virdee et al. |
| 2004/0172281 A1 | 9/2004 | Stanners |
| 2004/0188998 A1 | 9/2004 | Henthorn |
| 2004/0249745 A1 | 12/2004 | Baaren |
| 2005/0015280 A1 | 1/2005 | Gabel et al. |
| 2005/0033604 A1 | 2/2005 | Hogan |
| 2005/0033610 A1 | 2/2005 | Cunningham |
| 2005/0060201 A1 | 3/2005 | Connely, III et al. |
| 2005/0065821 A1 | 3/2005 | Kalies |
| 2005/0086081 A1 | 4/2005 | Brock-Fisher |
| 2005/0090425 A1 | 4/2005 | Reardan et al. |
| 2005/0102169 A1 | 5/2005 | Wilson |
| 2005/0125292 A1 | 6/2005 | Kassab et al. |
| 2005/0154627 A1* | 7/2005 | Zuzek et al. ............. 705/10 |
| 2005/0171815 A1 | 8/2005 | Vanderveen |
| 2005/0187793 A1 | 8/2005 | Myles |
| 2005/0197862 A1* | 9/2005 | Paterson et al. ........... 705/2 |
| 2005/0240473 A1 | 10/2005 | Ayers, Jr. et al. |
| 2005/0288972 A1 | 12/2005 | Marvin et al. |
| 2006/0015518 A1 | 1/2006 | Eletreby et al. |
| 2006/0020514 A1 | 1/2006 | Yered |
| 2006/0026041 A1 | 2/2006 | Ullman |

| | | | |
|---|---|---|---|
| 2006/0085230 | A1 | 4/2006 | Brill et al. |
| 2006/0149587 | A1 | 7/2006 | Hill, Sr. et al. |
| 2006/0149784 | A1 | 7/2006 | Tholl et al. |
| 2006/0184391 | A1 | 8/2006 | Barre et al. |
| 2006/0224415 | A1 | 10/2006 | Hudson et al. |
| 2006/0229915 | A1 | 10/2006 | Kosinski et al. |
| 2006/0247948 | A1 | 11/2006 | Ellis et al. |
| 2006/0259363 | A1 | 11/2006 | Jhetam et al. |
| 2006/0271398 | A1 | 11/2006 | Belcastro |
| 2006/0271405 | A1 | 11/2006 | Cipolle et al. |
| 2006/0287886 | A1 | 12/2006 | Kitazawa |
| 2007/0005402 | A1 | 1/2007 | Kennedy et al. |
| 2007/0050209 | A1 | 3/2007 | Yered |
| 2007/0088576 | A1 | 4/2007 | de Beus et al. |
| 2007/0124177 | A1 | 5/2007 | Engleson et al. |
| 2007/0136100 | A1 | 6/2007 | Daugherty et al. |
| 2007/0179957 | A1 | 8/2007 | Gibson et al. |
| 2007/0233525 | A1 | 10/2007 | Boyle |
| 2007/0233526 | A1 | 10/2007 | Hoffman et al. |
| 2007/0239493 | A1 | 10/2007 | Sweetland et al. |

FOREIGN PATENT DOCUMENTS

| | | |
|---|---|---|
| WO | 9106917 A1 | 5/1991 |
| WO | 9503569 A3 | 2/1995 |
| WO | 9725682 A1 | 7/1997 |
| WO | 9850871 A1 | 11/1998 |
| WO | 0039737 A1 | 7/2000 |
| WO | 2007025295 A2 | 3/2007 |

OTHER PUBLICATIONS

Anonymous, ACS to Demonstrate Electronic Health Record Solution Suite at MMIS 2007 Conference; EHR Tools Consolidate Data, Provide Useful Information at the Point of Care for Medicaid Providers, Payers, and Patients, PR Newswire, Aug. 13, 2007, New York, NY, USA.

Lamb, J., New Era of Electronic Medicine Management: E-Prescriptions, Britain's Traditionally Cautious National Health Service is Starting Trials for Online Prescription, with the Aim of Cutting Costs. Financial Times, London, Feb. 21, 2001, p. 6, London, United Kingdom.

Anonymous, Pharmacy Industry Leaders Launch Firm to Supply Real-Time Data. PR Newswire. Jul. 30, 2001, p. 1, New York, NY, USA.

Anonymous, Medic: On-line Goes In-House, Chain Store Age Executive, Jan. 1987, pp. 128-132. vol. 63, Issue 1, USA.

Anonymous, TechRx Announces Successful Beta Deployment of T-Rex. PR Newswire. May 13, 2002.

"Two automatic identification technology, neither new in the sense if being recent developments . . . " Patient Safety & Quality Healthcare [Online] Aug. 2005. URL: http://www.awarix.com.

"Subnotebooks, Phones, and More. St. Vincent's Gets on Track." Mobile Health Data [Online], Nov. 19, 2004. URL: http://www.awarix.com.

"Coping with Information Overload." The News Source for Healthcare Information Technology [Online] Nov. 2004. URL: http://www.awarix.com.

"St. Vincent's first to use Birmingham startup's information system." The Birmingham News [Online] Apr. 11, 2005. URL: http://www.awarix.com.

"St. Vincent's is Digital Flagship" D. Lockridge; Birmingham Medical News [Online] Sep. 2005. URL: http://www.awarix.com.

Non-Final Office Action for U.S. Appl. No. 12/570,939 mailed Oct. 27, 2011.

* cited by examiner

SYSTEMS AND METHODS FOR DETERMINING PRESCRIBING PHYSICIAN ACTIVITY LEVELS

FIELD OF THE INVENTION

Aspects of the invention relate generally to healthcare requests, and more particularly, to determining activity levels of physicians that are prescribing products associated with healthcare requests.

BACKGROUND OF THE INVENTION

In the healthcare field, certain healthcare providers, such as pharmacies and/or drug manufacturers, would like to determine an activity level of a physician for various business and/or marketing purposes. For example, a pharmacy or drug manufacturer may wish to determine whether a particular physician has an active practice prior to targeting that physician for marketing purposes. Therefore, a need exists for systems and methods for determining activity levels for physicians.

BRIEF DESCRIPTION OF THE INVENTION

Some or all of the above needs and/or problems may be addressed by certain embodiments of the invention. Embodiments of the invention may include systems and methods for determining prescribing physician activity levels. In one embodiment, a computer-implemented method for determining prescribing physician activity levels may be provided. Information associated with a plurality of healthcare transaction requests that are received during a designated time period from at least one healthcare provider computer for communication to one or more claims processor computers may be collected. A respective prescribing physician for each of the plurality of received healthcare transaction requests may be identified. For each identified physician, a respective activity measure for the designated time period may be calculated based upon a respective number of the healthcare transaction requests identifying the physician. In certain embodiments, the operations of the method may be performed by one or more computers associated with a service provider.

In accordance with another embodiment of the invention, a system for determining prescribing physician activity levels may be provided. The system may include at least one memory operable to store computer-executable instructions, and at least one processor configured to access the at least one memory. The at least one processor may be further configured to execute the computer-executable instructions to: collect information associated with a plurality of healthcare transaction requests that are received during a designated time period from at least one healthcare provider computer for communication to one or more claims processor computers; identify a respective prescribing physician for each of the plurality of received healthcare transaction requests; and calculate, for each identified physician and based upon a respective number of the healthcare transaction requests identifying the physician, a respective activity measure for the designated time period.

Additional systems, methods, apparatus, features, and aspects may be realized though the techniques of various embodiments of the invention. Other embodiments and aspects of the invention are described in detail herein with reference to the description and to the drawings and are considered a part of the claimed invention.

BRIEF DESCRIPTION OF THE DRAWINGS

Reference will now be made to the accompanying drawings, which are not necessarily drawn to scale, and wherein.

DETAILED DESCRIPTION

Figure 1:
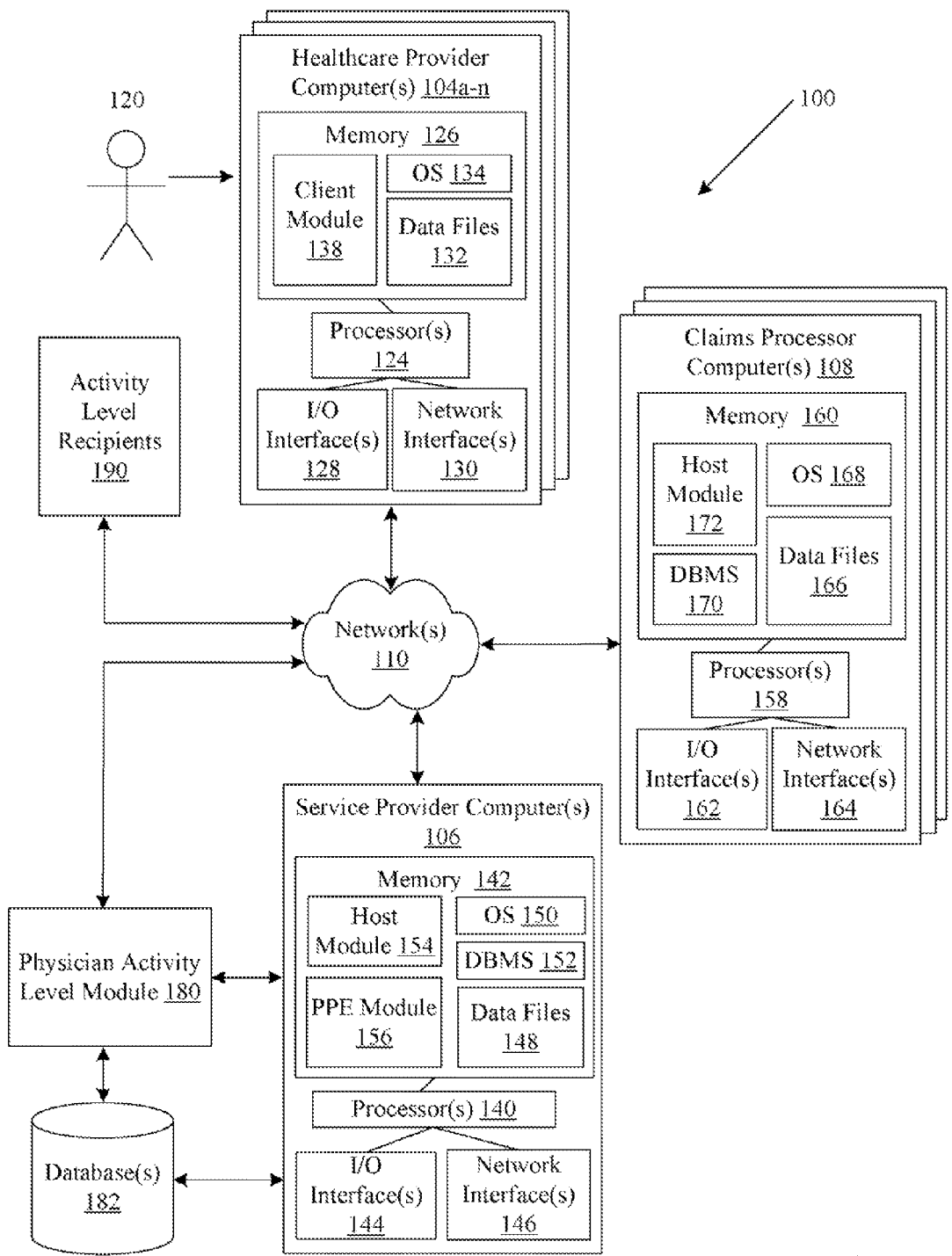
FIG. 1 illustrates an example overview of a system for determining prescribing physician activity levels, according to an example embodiment of the invention.

Embodiments of the invention now will be described more fully hereinafter with reference to the accompanying drawings, in which embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout.

Embodiments of the invention may include systems and methods for determining prescribing physician activity levels. According to an aspect of the invention, a physician's activity level may be determined or calculated based at least in part on a number of prescriptions written by the physician within one or more designated time periods, such as within the last seven (7) days or the last ninety (90) days. Information associated with a plurality of healthcare transaction requests, such as electronic prescription requests and/or healthcare claim transactions may be collected as the transaction requests are processed by and/or communicated through a service provider. Additionally, as desired, information associated with a plurality of healthcare transaction requests may be received from one or more external sources, such as third party service providers. Healthcare transaction requests for a designated time period may be determined, and a respective prescribing physician for each of the healthcare transaction requests may be identified. For each identified physician, a respective activity measure, such as an activity score, for the designated time period may be calculated based upon a number of the healthcare transaction requests identifying the physician. Once activity measures have been calculated for physicians, in certain embodiments, the physicians may be ranked relative to one another. As a result of the rankings, an activity level may be assigned to each physician.

Activity measures and/or activity levels for physicians may be utilized for a wide variety of purposes as desired in various embodiments of the invention. For example, new physicians that have begun to write prescriptions may be identified. As another example, physicians that have become inactive may be identified. As another example, potentially fraudulent and/or improper activities, such as a high level of activity by a sanctioned physician or a high level of activity outside of a medical expertise area of a physician, may be identified. As yet another example, various trends and/or market size calculations may be determined. As desired, a service provider that calculates activity measures and/or activity levels may provide the measures and/or levels to one or more recipients, such as one or more healthcare providers, drug manufacturers, etc. The recipient may utilize received information for a wide variety of suitable purposes, such as marketing purposes.

For purposes of this disclosure, a healthcare transaction request may include any suitable request associated with the request of healthcare products, such as prescription drugs, other prescription products, healthcare services, and/or healthcare procedures. One example of a healthcare transaction request is a healthcare claim transaction that is communicated from a healthcare provider, such as a pharmacy, to a service provider for routing or other communication to a claims processor for adjudication. Another example of a healthcare claim request is an electronic prescription request that is communicated from a first healthcare provider, such as a physician, through the service provider to a second healthcare provider, such as a pharmacy. A designated recipient of a healthcare transaction request may be referred to as a healthcare transaction processor. For example, a claims processor that receives a healthcare claim transaction or a healthcare provider (e.g., a pharmacy) that receives an electronic prescription request may be a healthcare transaction processor.

System Overview

An example system 100 for determining prescribing physician activity levels will now be described illustratively with respect to FIG. 1. As shown in FIG. 1, the system 100 may include any number of healthcare provider computers 104a-n, at least one service provider computer 106, and any number of claims processor computers 108a-n. As desired, each of the healthcare provider computers 104a-n, service provider computer(s) 106, and/or claims processor computers 108a-n may include one or more processing devices that may be configured for accessing and reading associated computer-readable media having stored thereon data and/or computer-executable instructions for implementing the various methods of the invention.

Additionally, in certain embodiments, the service provider computer 106 may include or otherwise be in communication with a physician activity level module 180 or physician activity level application, which may access and/or be in communication with one or more suitable data storage devices, 182. The physician activity level module 180 may receive information associated with a plurality of healthcare transaction requests, and the physician activity level module 180 may identify prescribing physicians for the transactions requests. As described in greater detail below, the physician activity level module 180 may then determine activity measures and/or activity levels for the prescribing physicians for any number of designated time periods.

Generally, network devices and systems, including one or more of the healthcare provider computers 104a-n, service provider computer 106, and claims processor computers 108a-n may include or otherwise be associated with suitable hardware and/or software for transmitting and receiving data and/or computer-executable instructions over one or more communications links or networks. These network devices and systems may also include any number of processors for processing data and executing computer-executable instructions, as well as other internal and peripheral components that are well known in the art. Further, these network devices and systems may include or be in communication with any number of suitable memory devices operable to store data and/or computer-executable instructions. By executing computer-executable instructions, each of the network devices may form a special purpose computer or particular machine. As used herein, the term "computer-readable medium" describes any form of suitable memory or memory device.

As shown in FIG. 1, the healthcare provider computers 104a-n, service provider computer 106, and claims processor computers 108a-n may be in communication with each other via one or more networks, such as network 110, which as described below can include one or more separate or shared private and public networks, including the Internet or a publicly switched telephone network. Each of these components—the healthcare provider computers 104a-n, service provider computer 106, and claims processor computers 108a-n, and the network 110—will now be discussed in further detail.

Any number of healthcare provider computer 104a-n may be provided. Each healthcare provider computer may be associated with a healthcare provider, for example, a pharmacy, physician's office, hospital, etc. A healthcare provider computer 104 may be any suitable processor-driven device that facilitates the processing of healthcare requests, such as requests made by patients, consumers, and/or other healthcare providers, and the communication of information associated with healthcare transaction requests (e.g., healthcare claim requests and/or electronic prescription orders) to the service provider computer 106. Examples of suitable processor-driven devices include, but are not limited to, a server computer, a mainframe computer, one or more networked computers, a desktop computer, a personal computer, a digital assistant, a personal digital assistant, a digital tablet, an Internet appliance, an application specific circuit, microcontroller, minicomputer, or any other processor-based device. In certain embodiments, the healthcare provider computer 104 may be a suitable point of sale device associated with a pharmacy or other healthcare provider. In other embodiments, the healthcare provider computer 104 may be suitable computer located at a physician's office that is utilized to prepare and/or approve electronic prescription orders for communication to a pharmacy. The execution of the computer-implemented instructions by the healthcare provider computer 104 may form a special purpose computer or other particular machine that is operable to facilitate the processing of healthcare requests and the communication of information associated with healthcare transaction requests to a service provider computer 106. Additionally, in certain embodiments of the invention, the operations and/or control of the healthcare provider computer 104 may be distributed amongst several processing components.

In addition to having one or more processors 124, the healthcare provider computer 104 may include one or more memory devices 126, one or more input/output ("I/O") interface(s) 128, and one or more network interface(s) 130. The memory devices 126 may be any suitable memory devices, for example, caches, read only memory devices, random access memory devices, magnetic storage devices, removable storage devices, etc. The memory devices 126 may store data, executable instructions, and/or various program modules utilized by the healthcare provider computer 104, for example, data files 132, an operating system 134, and/or a client module 138. The data files 132 may include any suitable data that facilitates the receipt and/or processing of healthcare requests by the healthcare provider computer 104 and the generation and/or processing of healthcare transaction requests that are communicated to the service provider computer 106. For example, the data files 132 may include, but are not limited to, healthcare information and/or contact information associated with one or more patients, information associated with the service provider computer 106, information associated with one or more pharmacies or other healthcare providers, information associated with one or more claims processors, and/or information associated with one or more healthcare transaction requests (e.g., prescription information, healthcare claim information, etc.). The operating system (OS) 134 may be a suitable software module that controls the general operation of the healthcare provider computer 104. The OS 134 may also facilitate the execution of other software modules by the one or more processors 124, for example, the client module 138. The OS 134 may be, but is not limited to, Microsoft Windows®, Apple OSX™, Linux, Unix, or a mainframe operating system. The client module 138 may be an Internet browser or other software, including a dedicated program, for interacting with the service provider computer 106. For example, a user 120 such as a pharmacist or other pharmacy employee, may utilize the client module 138 in preparing and providing a prescription claim request to the service processor computer 106 for delivery to the appropriate claims processor computer 108 for adjudication or other coverage/benefits determination. As another example, a user 120 such as a physician may utilize the client module 138 in preparing and providing an electronic prescription order to the service provider computer 106 for delivery to another healthcare provider computer 104 (e.g., pharmacy computer) for receipt by a pharmacy management system. The healthcare provider computer 104 may also utilize the client module 138 to retrieve or otherwise receive data, messages, or responses from the service provider computer 106 and/or other components of the system 100.

The one or more I/O interfaces 128 may facilitate communication between the healthcare provider computer 104 and one or more input/output devices, for example, one or more user interface devices, such as, a display, keypad, control panel, touch screen display, remote control, microphone, etc. that facilitate user interaction with the healthcare provider computer 104. For example, the one or more I/O interfaces 128 may facilitate entry of information associated with a healthcare transaction or healthcare claim request by an employee 120 of a healthcare provider, such as a pharmacy employee. The one or more network interfaces 130 may facilitate connection of the healthcare provider computer 104 to one or more suitable networks, for example, the network 110 illustrated in FIG. 1. In this regard, the healthcare provider computer 104 may receive and/or communicate information to other network components of the system 100, such as the service provider computer 106.

With continued reference to FIG. 1, the service provider computer 106 may include, but is not limited to, any suitable processor-driven device that is configured for receiving, processing, and fulfilling requests from a healthcare provider computer 104a-n and/or a claims processor computer 108a-n relating to prescription, pharmacy, benefits, and/or healthcare transactions and/or other activities. In certain embodiments, the service provider computer 106 may be a switch/router that routes healthcare claim transactions and/or other healthcare requests. For example, the service provider computer 106 may route billing requests and/or prescription claim requests (also referred to as "healthcare claim requests") communicated from the healthcare provider computer 104 to a claims processor computer 108, such as a pharmacy benefits manager (PBM), an insurer, a government payor, or a claims clearinghouse. Likewise, the service provider computer 106 may also route electronic prescription orders communicated from a first healthcare provider computer 104 (e.g., physician computer) to another healthcare provider computer 104 (e.g., a pharmacy computer) for receipt into a pharmacy management system. In certain embodiments, the service provider computer 106 may include a suitable host server, host module, or other software that facilitates the receipt of a healthcare transaction request from a healthcare provider computer 104 and/or the routing of the received healthcare transaction request to a claims processor computer 108. Any number of healthcare provider computers and/or claims processor computers may be in communication with the service provider computer 106 as desired in various embodiments of the invention.

The service provider computer 106 may include any number of special purpose computers or other particular machines, application specific circuits, microcontrollers, personal computers, minicomputers, mainframe computers, servers, networked computers, and/or other processor driven devices. In certain embodiments, the operations of the service provider computer 106 may be controlled by computer-executed or computer-implemented instructions that are executed by one or more processors associated with the service provider computer 106 to form a special purpose computer or other particular machine that is operable to facilitate the receipt, routing, and/or processing of healthcare transaction requests. The one or more processors that control the operations of the service provider computer 106 may be incorporated into the service provider computer 106 and/or in communication with the service provider computer 106 via one or more suitable networks. In certain embodiments of the invention, the operations and/or control of the service provider computer 106 may be distributed amongst several processing components.

Similar to the healthcare provider computer 104, the service provider computer 106 may include one or more processors 140, one or more memory devices 142, one or more input/output ("I/O") interface(s) 144, and one or more network interfaces 146. The one or more memory devices 142 may be any suitable memory devices, for example, caches, read only memory devices, random access memory devices, magnetic storage devices, removable memory devices, etc. The one or more memory devices 142 may store data, executable instructions, and/or various program modules utilized by the service provider 106, for example, data files 148, an operating system ("OS") 150, the host module 154, a pre- and post-edit (PPE) module 156, and a database management system ("DBMS") 152 to facilitate management of data files 148 and other data stored in the memory devices 142 and/or one or more databases 182. The OS 150 may be, but is not limited to, Microsoft Windows®, Apple OSX™, Linux, Unix, or a mainframe operating system.

The PPE module 156 may be operable to perform one or more pre-edits on a received healthcare transaction request prior to routing or otherwise communicating the received healthcare transaction request to a suitable claims processor computer 108 (for a claim request) or healthcare provider computer 104 (for an electronic prescription order). Additionally, the PPE module 156 may be operable to perform one or more post-edits on an adjudicated reply or response that is received from a claims processor computer 108 (or alternatively, a healthcare provider computer 104) for a healthcare claim transaction prior to routing the adjudicated reply to a healthcare provider computer 104. A wide variety of different pre-edits and/or post-edits may be performed as desired in various embodiments of the invention. In certain embodiments, the physician activity level module 180 may be incorporated into the PPE module 156 and/or in communication with the PPE module 156.

According to an embodiment of the invention, the data files 148 may store healthcare transaction records associated with communications received from various healthcare provider computers 104 and/or various claims processor computers 108. The data files 148 may also store any number of suitable routing tables that facilitate determining the destination of communications received from a healthcare provider computer 104 or claims processor computer 108. The host module 154 may receive, process, and respond to requests from the client module 138 of the healthcare provider computer 104, and may further receive, process, and respond to requests of the host module 172 of the claims processor computer 108. The service provider computer 106 may include additional program modules for performing other processing methods described herein. Those of ordinary skill in the art will appreciate that the service provider computer 106 may include alternate and/or additional components, hardware or software without departing from example embodiments of the invention.

A physician activity level module 180 or physician activity level application may also be operative with the service provider computer 106. The physician activity level module 180 may include computer-executable instructions for processing healthcare transaction requests and/or replies to healthcare transaction requests in order to determine activity measures (e.g., activity scores) and/or activity levels for prescribing physicians. The physician activity level module 180 may further be operable to rank physicians relative to one another in accordance with or in association with determining their activity levels. According to an aspect of the invention, the physician activity level module 180 may collect information associated with healthcare transaction requests and/or replies in real-time or near real-time as the requests and/or replies are routed or communicated through the service provider computer 106. In certain embodiments, the physician activity level module 180 may be or include a pre-edit service that is performed for a healthcare transaction request in order to collect data associated with the request. Additionally or alternatively, the physician activity level module 180 may be or include a post-edit service that is performed for a reply to healthcare transaction request in order to collect data associated with the reply.

In addition to or as an alternative to collecting information as requests and/or replies are processed or communicated through the service provider computer 106, the physician activity level module 180 and/or the service provider computer 106 may collect information associated with healthcare transaction requests and/or replies from any number of external sources. For example, information may be collected from other service providers that are configured to route claims and/or prescription requests, from any number of healthcare providers, and/or from any number of claims processors.

Collected information associated with healthcare transaction requests and/or replies may be stored in any number of suitable databases 182 as desired in various embodiments of the invention. The stored information may be organized or sorted in accordance with any number of suitable parameters, such by originating healthcare provider (e.g., pharmacy, physician, etc.) for transaction requests or by prescribing physician for transaction requests. For example, the physician activity level module 180 may identify a prescribing physician associated with a healthcare transaction request or reply when the transaction request/reply is processed by the physician activity level module 180, and the physician activity level module 180 may store information associated with the request/reply in accordance with the identified physician and/or an identifier of the transaction, such as a prescription number or service reference number. In certain embodiments, a prescribing physician may be identified by a prescriber identifier (e.g., a National Provider Identifier (NPI), Drug Enforcement Agency (DEA) number, etc.) or other prescriber identifying information included in a healthcare request/reply. In this regard, prescriptions associated with a particular physician may be easily identified and/or accessed by the physician activity level module 180. Additionally, the physician activity level module 180 may identify and/or eliminate duplicate entries within the databases 182. For example, if a database record for a particular prescription number written by a physician is included in the database from a previously processed electronic prescription request, then a new record will not be generated for a healthcare claim transaction for the same prescription. As desired, the existing record may be modified or updated when additional information associated with the prescription is identified.

As an alternative to storing individual information for each transaction, a number of healthcare transaction requests identifying a physician may be periodically determined or calculated, and the number may be stored in association with the physician. For example, at the end of each day, a respective number of prescriptions associated with a plurality of physicians may be calculated or determined, and the numbers may be stored in association with the identified physicians.

Once data is collected by the physician activity level module 180, the physician activity level module 180 may utilize the collected data in association with any number of processing rules to calculate or determine physician activity measures and/or activity levels. Healthcare transaction request data for one or more designated time periods may be accessed and/or otherwise obtained for analysis by the physician activity level module 180. In certain embodiments, a designated time period may be a historical time period. Any number of designated time periods may be utilized as desired in various embodiments of the invention, such as a relatively short term time period (e.g., a seven (7) day history, a fourteen (14) day history, etc.) and/or a longer term time period (e.g., a thirty (30) day history, a ninety (90) day history, etc.). Once healthcare transaction request data has been accessed or obtained for a designated time period, the respective healthcare transaction requests for each physician may be identified. Information included in the transaction requests for a physician may then be utilized to calculate an activity measure for the physician during the designated time period. A wide variety of various rules, parameters, and/or formulas may be utilized to calculate an activity measure for a physician. For example, an activity measure may be based upon a number of prescriptions written by a physician for a designated time period. As desired, an activity measure may additionally be based upon a number of pharmacies that received electronic prescription requests and/or that submitted healthcare claim requests identifying the physician. In this regard, the artificial inflation of an activity measure for a particular physician based upon a pharmacy failing to accurately complete or update a prescriber field for healthcare claim transactions may be minimized and/or avoided. One example formula for calculating a physician activity measure for a designated time period is set forth in equation 1 below:

$$ActivityScore = (\text{\# of Prescriptions}) \cdot \left[2 - \frac{1}{\text{\#ofPharmacies}}\right] \quad (1)$$

With reference to equation 1, an activity measure for a physician may be calculated by multiplying the number of prescriptions for the designated time period that identify a physician by the result of two minus one over the total number of pharmacies that submitted and/or received healthcare requests that identify the physician. The formula set forth in equation 1 is provided by way of example only, and it will be appreciated that any number of formulas and/or rules may be utilized as desired to determine a physician activity measure for a designated time period. Other example parameters that may be utilized in a calculation include, but are not limited to, geographical information associated with the transactions (e.g., geographical information for the healthcare providers), product information (e.g., therapeutic class, drug classification, product identifiers, product names, etc.) associated with the transactions, etc.

Once physician activity measures have been calculated for a plurality of physicians, the physician activity level module 180 may rank the physicians relative to one another and/or relative to a set or predetermined value based upon their calculated activity measures. A wide variety of different processing rules may be utilized as desired to rank physicians. In one example embodiment, the activity measures of the physicians may be placed in order from lowest to highest (or highest to lowest) and divided into a predetermined number of groups having an approximately equal number of entries. A prescriber activity level may then be attributed to each group. For example, the activity measures may be divided into approximately ten (10) groups. A first activity level of one may be attributed to the first group, a second activity level of two may be attributed to the second group, and so on. The activity level for a physician may be indicative of how active the physician is within a designated time period relative to other physicians.

Physician activity levels and/or activity measures may be utilized for a wide variety of different purposes as desired in various embodiments of the invention. For example, a physician activity level may be utilized to determine whether a particular physician is a new physician. As another example, physicians that do not have an associated activity level may be identified. In this regard, physicians that have become inactive (e.g., retired, leave of absence, etc.) may be identified. As desired, activity levels for multiple time periods or for relatively long time periods may be analyzed in order to determine whether a physician has become inactive. For example, a physician may not be determined to be inactive if they have no associated transaction requests within the last seven days; however, the physician may be determined to be inactive if they have no associated transaction requests within the last ninety days. As desired, a status of a physician (e.g., an active/inactive status) may be verified and/or updated based upon the analysis of calculated physician activity levels.

As another example, physician activity levels may be utilized to identify improper and/or potentially fraudulent activity. For example, if a activity level for a sanctioned or suspended physician is greater than a threshold activity level, then a determination may be made that the physician is violating the terms of a sanction or suspension. As another example, the types of drugs and/or products that are prescribed by a physician may be identified by National Drug Codes, Universal Product Codes, and/or other identifiers. Additionally, a specialty or other classification of the physician may be identified. The identified specialty and/or types of products may be utilized in associated with the activity level of the physician to identify potentially fraudulent activity. For example, potentially fraudulent activity may be identified if a veterinarian is writing a relatively large number of prescriptions for drugs intended for human use and/or consumption. Additionally, physician activity level data may be utilized to determine or estimate relative practice sizes and/or geographical areas of physicians and/or to determined prescription trends amongst physicians. As desired, the physician activity measures and/or levels may be utilized for a wide variety of other purposes.

In certain embodiments, the physician activity level module 180 may provide information associated with calculated activity measures, activity levels, and/or the analysis of the measures/levels to one or more recipients, such as drug manufactures, pharmacies, etc. For example, the physician activity level module 180 may communicate or direct the communication of activity data to any number of activity level recipients 190 (e.g., a pharmacy chain back office computer, a drug manufacturer, etc.) and/or other components of the system 100, such as a healthcare provider computer 104 or a claims processor computer 108. In certain embodiments, the physician activity level module 180 and/or an associated reporting module may generate one or more reports associated with physician activity levels. A wide variety of different techniques and/or software programs may be utilized to format a generated report. For example, a report may be formatted as a comma-separated-value (csv) file, as a spreadsheet file, as a word processor file, as a text file, etc. Additionally, a wide variety of different communication techniques may be utilized to communicate physician activity information and/or reports to the recipient, including but not limited to, email, short message service (SMS) messaging, other electronic communications, snail mail, etc. Additionally, in certain embodiments, information may be made available for download from an appropriate web site or server, such as a web site hosted by the service provider computer 106. As desired, a recipient may utilize received activity data for a wide variety of marketing and/or business purposes. For example, a pharmacy or drug manufacturer may identify a new physician and provide marketing data and/or special offers to the physician.

The data storage devices 182 may be operable to store information associated with various rules and/or edits that may be utilized by the physician activity level module 180 to process healthcare transaction requests and/or to calculate activity measures and/or levels. Additionally, the data storage devices 182 may be operable to store information associated with healthcare transaction requests and/or processing performed by the physician activity level module 180. In certain embodiments, the data storage devices 182 may additionally store reports associated with the healthcare transaction requests, processing of the healthcare transaction requests, and determined activity level information. The data storage devices 182 may be accessible by the physician activity level module 180 and/or the service provider computer 106.

The operations of the physician activity level module 180 and/or the data storage devices 182 are described in greater detail below with reference to FIGS. 2-4. Additionally, although the physician activity level module 180 is described as calculating activity information for individual physicians, it will be appreciated that activity measures and/or activity levels may be similarly calculated for groups of physicians in a similar manner.

With continued reference to the service provider computer 106, the one or more I/O interfaces 144 may facilitate communication between the service provider computer 106 and one or more input/output devices, for example, one or more user interface devices, such as, a display, keypad, control panel, touch screen display, remote control, microphone, etc. that facilitate user interaction with the service provider computer 106. The one or more network interfaces 146 may facilitate connection of the service provider computer 106 to one or more suitable networks, for example, the network 110 illustrated in FIG. 1. In this regard, the service provider computer 106 may communicate with other components of the system 100.

With continued reference to FIG. 1, the claims processor computer 108 may be any suitable processor-driven device that facilitates receiving, processing, and/or fulfilling healthcare claim transactions and/or healthcare claim requests received from the service provider computer 106. For example, the claims processor computer 108 may be a processor-driven device associated with a pharmacy benefits manager (PBM), an insurer, a government payor, or a claims clearinghouse. As desired, the claims processor computer 108 may include any number of special purpose computers or other particular machines, application specific circuits, microcontrollers, personal computers, minicomputers, mainframe computers, servers, and the like. In certain embodiments, the operations of the claims processor computer 108 may be controlled by computer-executed or computer-implemented instructions that are executed by one or more processors associated with the claims processor computer 108 to form a special purpose computer or other particular machine that is operable to facilitate the receipt, processing, and/or fulfillment of healthcare claim transaction requests received from the service provider computer 106. The one or more processors that control the operations of the claims processor computer 108 may be incorporated into the claims processor computer 108 and/or in communication with the claims processor computer 108 via one or more suitable networks. In certain embodiments of the invention, the operations and/or control of the claims processor computer 108 may be distributed amongst several processing components.

Similar to other components of the system 100, the claims processor computer 108 may include one or more processors 158, one or more memory devices 160, one or more input/output ("I/O") interface(s) 162, and one or more network interfaces 164. These components may be similar to those for the healthcare provider computer 104 and/or the service provider computer. The one or more memory devices 160 may store data, executable instructions, and/or various program modules utilized by the claims processor computer 108, for example, data files 166, an operating system ("OS") 168, a database management system ("DBMS") 170, and a host module 172. The data files 166 may include any suitable information that is utilized by the claims processor computer 108 to process healthcare claim transactions, for example, patient profiles, patient insurance information, other information associated with a patient, information associated with a healthcare provider, etc. The operating system (05) 168 may be a suitable software module that controls the general operation of the claims processor computer 108 and/or the execution of other software modules by the one or more processors 158, for example, the DBMS 170 and/or the host module 172. The OS 150 may be, but is not limited to, Microsoft Windows®, Apple OSX™, Linux, Unix, or a mainframe operating system. The DBMS 170 may be a suitable software module that facilitates access and management of one or more databases that are utilized to store information that is utilized by the claims processor computer 108 in various embodiments of the invention. The host module 172 may initiate, receive, process, and/or respond to requests, such as healthcare claim transactions or claim requests, from the host module 154 of the service provider 106. The claims processor computer 108 may include additional program modules for performing other pre-processing or post-processing methods described herein. Those of ordinary skill in the art will appreciate that the claims processor 108 computer may include alternate and/or additional components, hardware or software without departing from example embodiments of the invention.

The network 110 may include any telecommunication and/or data network, whether public, private, or a combination thereof, including a local area network, a wide area network, an intranet, the Internet, intermediate hand-held data transfer devices, and/or any combination thereof and may be wired and/or wireless. The network 110 may also allow for real-time, off-line, and/or batch transactions to be transmitted between or among the healthcare provider computer 104, the service provider computer 106, and the claims processor computer 108. Due to network connectivity, various methodologies as described herein may be practiced in the context of distributed computing environments. Although the service provider computer 106 is shown for simplicity as being in communication with the healthcare provider computer 104 or the claims processor computer 108 via one intervening network 110, it is to be understood that any other network configuration is possible. For example, intervening network 110 may include a plurality of networks, each with devices such as gateways and routers for providing connectivity between or among networks 110. Instead of or in addition to a network 110, dedicated communication links may be used to connect the various devices in accordance with an example embodiment of the invention. For example, the service provider computer 106 may form the basis of network 110 that interconnects the healthcare provider computer 104 and the claims processor computer 108.

Those of ordinary skill in the art will appreciate that the system 100 shown in and described with respect to FIG. 1 is provided by way of example only. Numerous other operating environments, system architectures, and device configurations are possible. Other system embodiments can include fewer or greater numbers of components and may incorporate some or all of the functionality described with respect to the system components shown in FIG. 1. For example, in one embodiment, the service provider computer 106 (or other computer) may be implemented as a specialized processing machine that includes hardware and/or software for performing the methods described herein. In addition, at least a portion of the processor and/or processing capabilities of the service provider computer 106 and/or the physician activity level module 180, may be implemented as part of the claims processor computer 108. Accordingly, embodiments of the invention should not be construed as being limited to any particular operating environment, system architecture, or device configuration.

Operational Overview

Figure 2A:
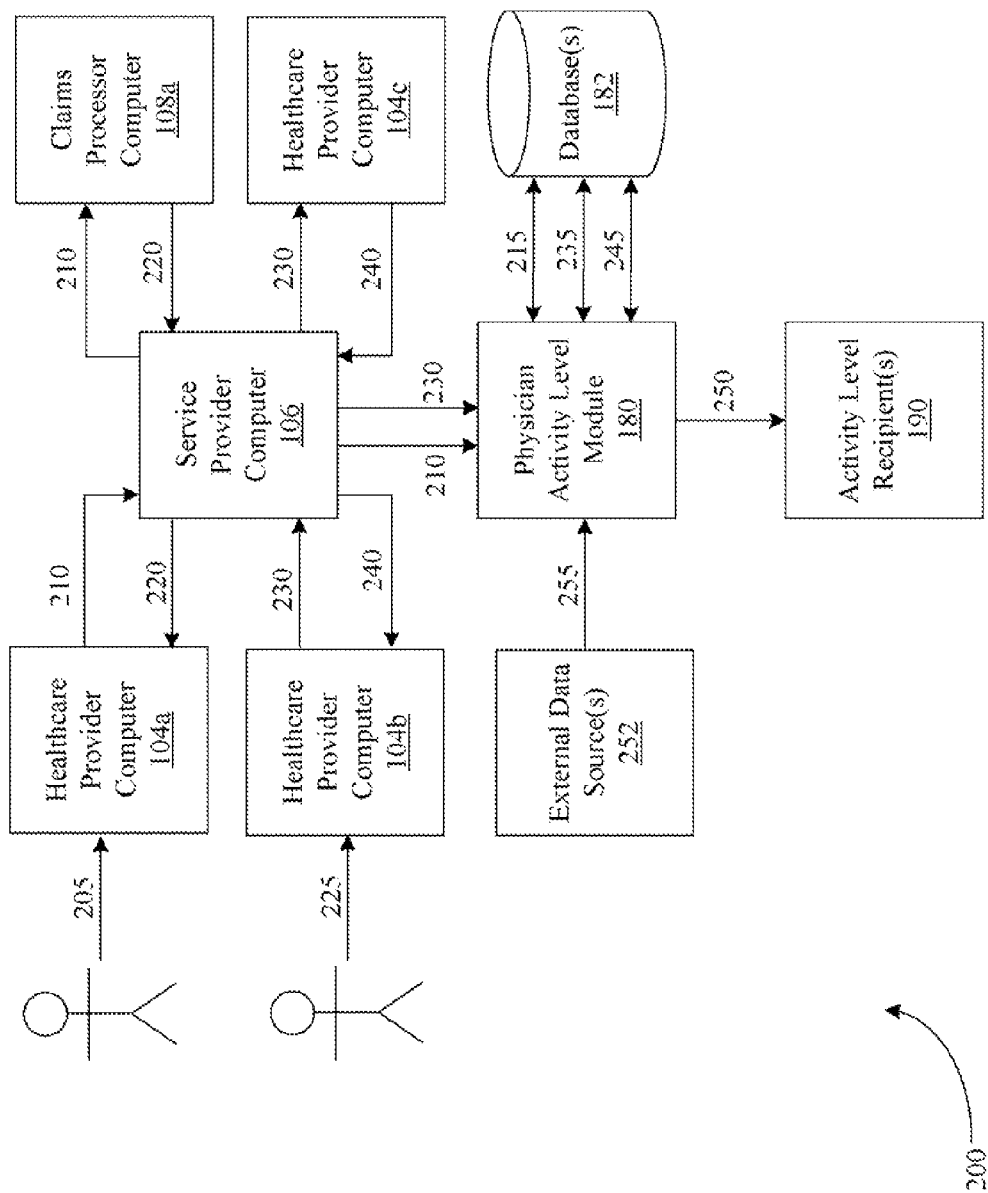
FIGS. 2A and 2B illustrate example block diagrams for processing healthcare claim transaction in order to determine prescribing physician activity levels, according to illustrative embodiments of the invention.
Figure 2B:
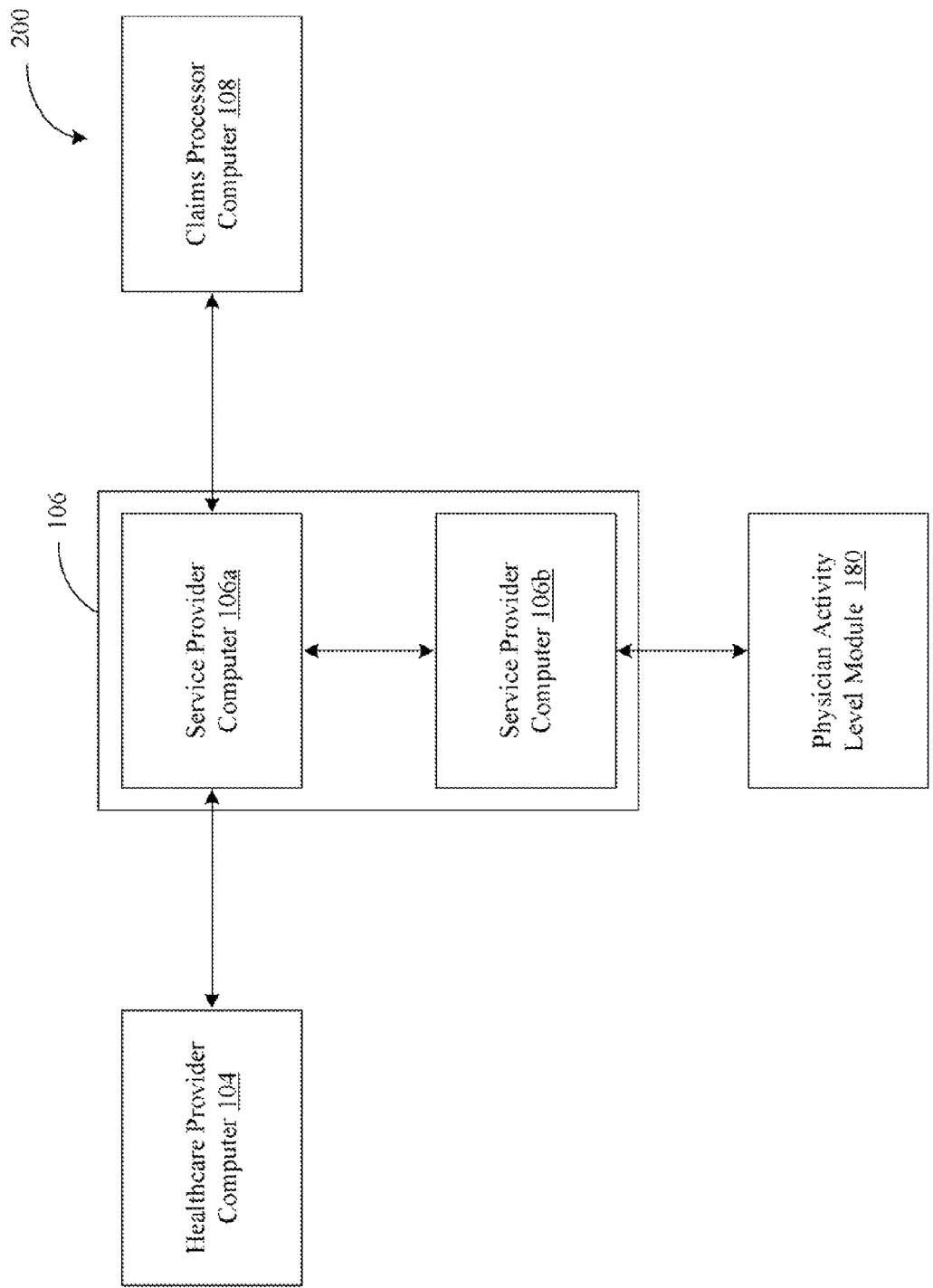

FIGS. 2A and 2B illustrate example block diagrams and data flows 200 for processing healthcare claim transactions in order to determine prescribing physician activity levels, according to illustrative embodiments of the invention. With reference to FIG. 2A, a healthcare provider computer, such as a first healthcare provider computer 104a illustrated in FIG. 1, may receive a healthcare request 205 (e.g., a prescription order) from a patient, such as a healthcare request 205 for a prescription drug or product. The healthcare request 205 may be received in-person or electronically as desired in various embodiments of the invention. For example, a patient may request a medication product at a pharmacy or physician's offices. As another example, a patient may communicate a healthcare request 205 to the healthcare provider computer 104a via one or more suitable network connections. For example, a purchase request for a product may be communicated to the healthcare provider computer 104a from a customer computer via a web portal hosted by the healthcare provider computer 104a.

The healthcare provider computer 104a (e.g., a pharmacy computer, a physician computer, etc.) may utilize the received healthcare request 205 to generate a healthcare claim transaction 210. The generated healthcare claim transaction 210 may be communicated by the healthcare provider computer 104a to the service provider computer 106. According to an example embodiment of the invention, the healthcare claim transaction 210 may be in accordance with a version of a National Council for Prescription Drug Programs (NCPDP) Telecommunication or SCRIPT Standard, although other standards may be utilized as well. The claim transaction 210 may include a Banking Identification Number (BIN) and/or a Processor Control Number (PCN) for identifying a particular claims processor computer or payor, such as a first claims processor computer 108a illustrated in FIG. 1, as a destination for the healthcare claim transaction 210. In addition, the healthcare claim request may also include information relating to the patient, payor, prescriber, healthcare provider, and/or the prescribed or administered drug or product. As an example, the healthcare claim transaction 210 received by the service provider computer 106 may include one or more of the following information:

Payor ID/Routing Information
    BIN Number (i.e. Banking Identification Number) and/or Processor Control Number (PCN) that designates a destination of the healthcare claim transaction Patient Information
    Name (e.g., Patient Last Name, Patient First Name, etc.)
    Date of Birth of Patient
    Age of Patient
    Gender
    Patient Address (e.g., Street Address, Zip Code, etc.)
    Patient Contact Information (e.g., Patient Telephone Number, email address, etc.)
    Patient ID or other identifier Insurance/Coverage Information
    Cardholder Name (e.g., Cardholder First Name, Cardholder Last Name)
    Cardholder ID and/or other identifier (e.g., person code)
    Group ID and/or Group Information
    State Payor Information Prescriber Information
    Primary Care Provider ID or other identifier (e.g., NPI code)
    Primary Care Provider Name (e.g., Last Name, First Name)
    Prescriber ID or other identifier (e.g., NPI code, DEA number)
    Prescriber Name (e.g., Last Name, First Name)
    Prescriber Contact Information (e.g., Telephone Number)

Pharmacy or other Healthcare Provider Information (e.g., store name, chain identifier, etc.)
Pharmacy or other Healthcare Provider ID (e.g., National Provider Identifier (NPI) code)

Claim Information
    Drug or product information (e.g., National Drug Code (NDC))
    Prescription/Service Reference Number
    Date Prescription Written
    Quantity Dispensed
    Number of Days Supply
    Diagnosis/Condition
    Pricing information for the drug or product (e.g., network price, Usual & Customary price)
    One or more NCPDP Message Fields
    One or more Drug Utilization (DUR) Codes
    One or more Dispense as Written (DAW) Codes or other DAW information Date of Service.

Once the healthcare claim transaction 210 is received by the service provider computer 106, the service provider computer 106 may process the healthcare claim transaction 210. As desired, the service provider computer 106 may perform one or more pre-edits on the healthcare claim transaction 210. If a physician activity level service or analysis is activated, the service provider computer 106 may communicate a copy of the claim transaction 210 and/or information included in the transaction 210 to a physician activity level module, such as the physician activity level module 180 illustrated in FIG. 1, for storage and/or analysis. The physician activity level module 180 may store information 215 associated with the claim transaction 210 in one or more suitable databases, such as the databases 182 illustrated in FIG. 1. In certain embodiments, the physician activity level module 180 may identify a prescribing physician associated with the claim transaction 210 and information may be stored in association with the identified physician.

The service provider computer 106 may additionally route or otherwise communicate the healthcare claim transaction 210 or a copy thereof to the appropriate claims processor computer 108a for adjudication. According to an example embodiment, the service provider 106 may utilize at least a portion of the information included in the healthcare claim transaction 210, such as a BIN/PCN, to determine the appropriate claims processor computer 108a to route the healthcare claim transaction 210 to. The service provider computer 106 may also include a routing table, perhaps stored in memory, for determining which claims processor computer 108a to route the healthcare claim transaction request 210 to. The claims processor computer 108a may receive and process the healthcare claim transaction 210. For example, the claims processor computer 108a may determine benefits coverage for the healthcare claim transaction 210. An adjudicated reply 220 or other response to the claim transaction 210 may be generated by the claims processor computer 108a and communicated to the service provider computer 106. The adjudicated reply 220 typically indicates whether the claim was paid or rejected by the claims processor computer 108a. The service provider computer 106 may optionally perform a wide variety of post-edits on the adjudicated reply 220. In certain embodiments, a copy of the adjudicated reply 220 or information included in the reply 220 may be communicated to the physician activity level module 180 for processing in a similar manner as the processing performed for the healthcare claim transaction 210. The service provider computer 106 may then route or otherwise communicate the adjudicated reply 220 to the healthcare provider computer 104a.

With continued reference to FIG. 2A, a healthcare request associated with an electronic prescription order may also be received and processed by the service provider computer 106. A healthcare provider computer associated with a physician's office, such as a second healthcare provider computer 104b illustrated in FIG. 1, may optionally receive a healthcare request 205 (e.g., a prescription order) from a patient, such as a healthcare request 225 for a prescription drug or product. The healthcare request 225 may be received in-person or electronically as desired in various embodiments of the invention. For example, a patient may request a medication product at a physician's offices. As another example, a patient may communicate a healthcare request 225 to the healthcare provider computer 104b via one or more suitable network connections. For example, a request for a prescription product may be communicated to the healthcare provider computer 104b from a customer computer via a web portal hosted by the healthcare provider computer 104b.

The healthcare provider computer 104b may utilize the received healthcare request 225 to generate an electronic prescription order 230. The generated electronic prescription order 230 may be communicated by the healthcare provider computer 104b to the service provider computer 106. The electronic prescription order 230 may include one or more of the following healthcare transaction information: a pharmacy identifier for identifying another healthcare provider computer 104c (e.g., a pharmacy computer) as a destination of the electronic prescription order 230; prescriber/healthcare provider information; prescribed drug or product information; diagnosis/ailment information; and/or patient information. For example, prescriber/healthcare provider information may include a name and/or contact information (e.g., address and/or telephone number) and an identifier for the prescriber (e.g., a National Provider Identifier (NPI) code or Drug Enforcement Administration (DEA) number). The prescribed drug or product information may include a name of a prescribed drug or product, a drug/product identifier (e.g., a National Drug Code (NDC)), or other information such as quantity, refills, form (e.g., tablet, gel, etc.), dosage instructions, and/or date for the prescription. The diagnosis/ailment information may include certain codes or identifiers to identify the condition(s) that the service or product is being prescribed to treat. The patient information may include a name and/or contact information for the patient, as well as other patient information such as a date of birth (DOB).

Once the electronic prescription order 230 is received by the service provider computer 106, the service provider computer 106 may process the electronic prescription order 230. As desired, the service provider computer 106 may perform one or more pre-edits on the electronic prescription order 230. If a physician activity level service or analysis is activated, the service provider computer 106 may communicate a copy of the electronic prescription order 230 and/or information included in the order 230 to the physician activity level module 180 for storage and/or analysis. The physician activity level module 180 may store information 235 associated with the order 230 in the databases 182 in a similar manner as that performed for the claim transaction 210. The service provider computer 106 may then route or otherwise communicate the order 230 or a copy thereof to a recipient healthcare provider computer 104c designated by the order 230. The recipient computer 104c may receive and process the electronic prescription order 230. In certain embodiments, the healthcare provider computer 104c may communicate a message 240 indicating receipt of the order 230 to the service provider computer 106. As desired, the message 240 or a copy thereof may be processed by the physician activity level module 180. The message 240 may then be routed or otherwise communicated to the healthcare provider computer 104b that submitted the order 230.

As discussed above, the physician activity level module 180 may collect information associated with healthcare transaction requests, including the claim transaction 210 and the electronic prescription order 230, as the transaction requests are routed or communicated through the service provider computer 106. Additionally, as desired, information 255 associated with healthcare transaction requests that are not routed through the service provider computer 106 may be received by the physician activity level module 180 from one or more external data sources 252, such as other service providers, claims processors, and/or healthcare providers.

Once information associated with healthcare transaction requests has been collected and/or received by the physician activity level module 180, the physician activity level module 180 may access one or more parameters 245 associated with calculating physician activity measures and/or levels from the databases 182, such as one or more designated time periods and/or formulas. The physician activity level module 180 may then calculate physician activity measures and/or levels for any number of prescribing physicians in a similar manner as that discussed above in FIG. 1 and that discussed in greater detail below with reference to FIG. 4. Information 250 and/or reports associated with the calculated physician activity measures and/or levels may then be communicated by the physician activity level module 180 or at the direction of the physician activity level module 180 to one or more activity level recipients, such as the recipients 190 illustrated in FIG. 1.

It will be appreciated that variations of the data flow 200 illustrated in FIG. 2A may be utilized in accordance with various embodiments of the invention. For example, as shown in FIG. 2B, the service provider computer 106 may be comprised of two or more distinct service provider computers 106a and 106b that are in communication with each other. Service provider computer 106a may be operative with one or more healthcare provider computers and claims processor computers, such as the healthcare provider computer 104 and claims processor computer 108 illustrated in FIG. 1. However, service provider computer 106b may have a data processing arrangement with service provider computer 106a. Under the data processing agreement, the service provider computer 106a may be permitted to utilize or offer services of the service provider computer 106b, including those of the physician activity level module 180. For example, a first service provider may communicate healthcare transaction requests and/or other information to a second service provider for processing.

Figure 3:
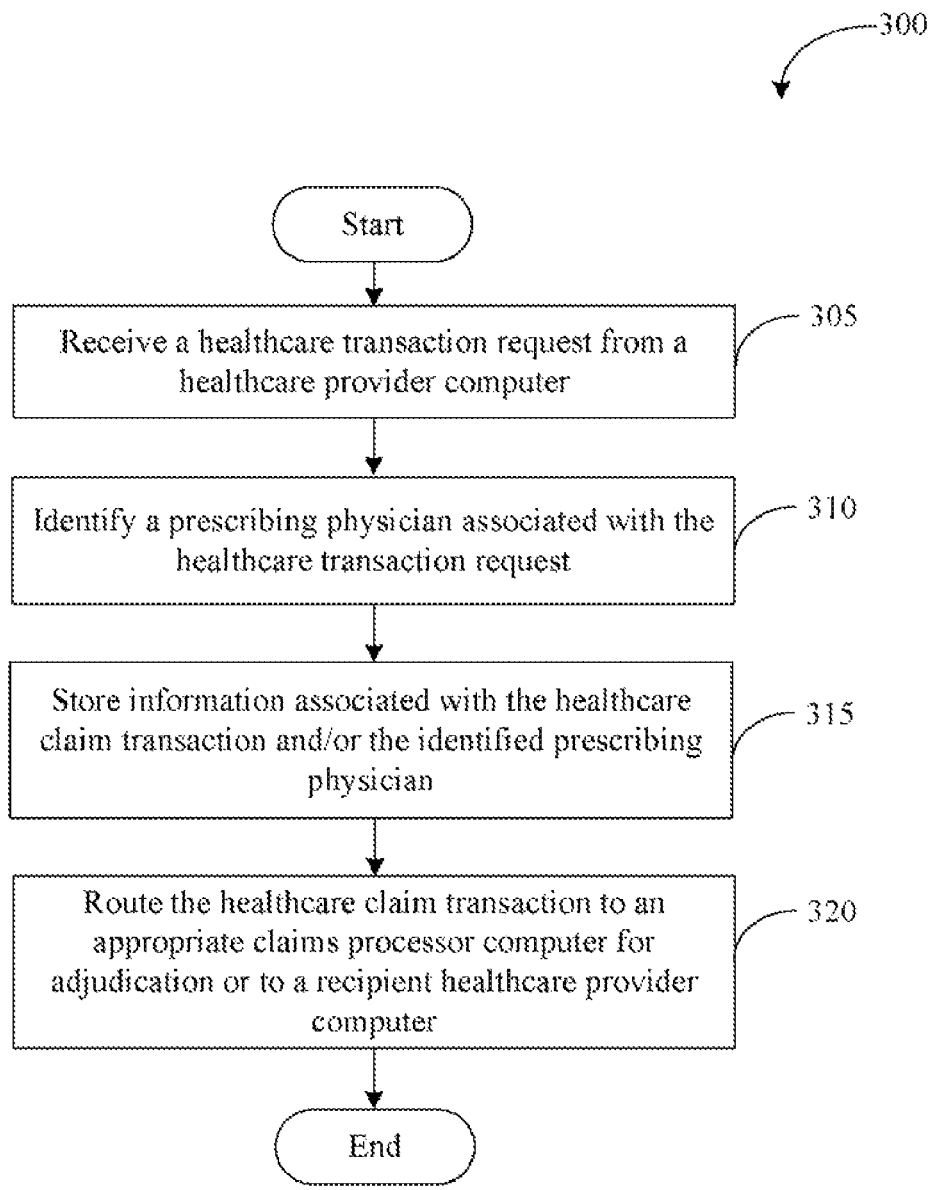
FIG. 3 is a flow chart of an example method for collecting information associated with healthcare claim transactions, according to an illustrative embodiment of the invention.

FIG. 3 is a flow chart of an example method 300 for collecting information associated with healthcare claim transactions, according to an illustrative embodiment of the invention. The method 300 may be performed by a suitable service provider computer and/or an associated physician activity level module, such as the service provider computer 106 and physician activity level module 180 illustrated in FIG. 1. The method 300 may begin at block 305.

At block 305, a healthcare transaction request, such as a healthcare claim transaction or an electronic prescription order, may be received from a healthcare provider computer, such as the healthcare provider computer 104 illustrated in FIG. 1. As desired, a wide variety of pre-edits may be performed on the received healthcare transaction request. For example, the healthcare transaction request may be processed by a physician activity level module 180.

At block 310, which may be optional in certain embodiments of the invention, a prescribing physician associated with or designated by the healthcare transaction request may be identified. For example, information included in the transaction request, such as a prescriber identifier (e.g., a NPI code, DEA number, etc.), may be analyzed in order to identify a prescribing physician. Information associated with the healthcare claim transaction and/or the identified prescribing physician may then be stored at block 315. The healthcare claim transaction may then be routed or otherwise communicated to a recipient at block 320, such as an appropriate claims processor computer or another healthcare provider computer. In this regard, information associated with the healthcare transaction request may be collected in real time or near real time as the transaction request is processed and/or routed by the service provider computer 106.

The method 300 may end following block 320.

Figure 4:
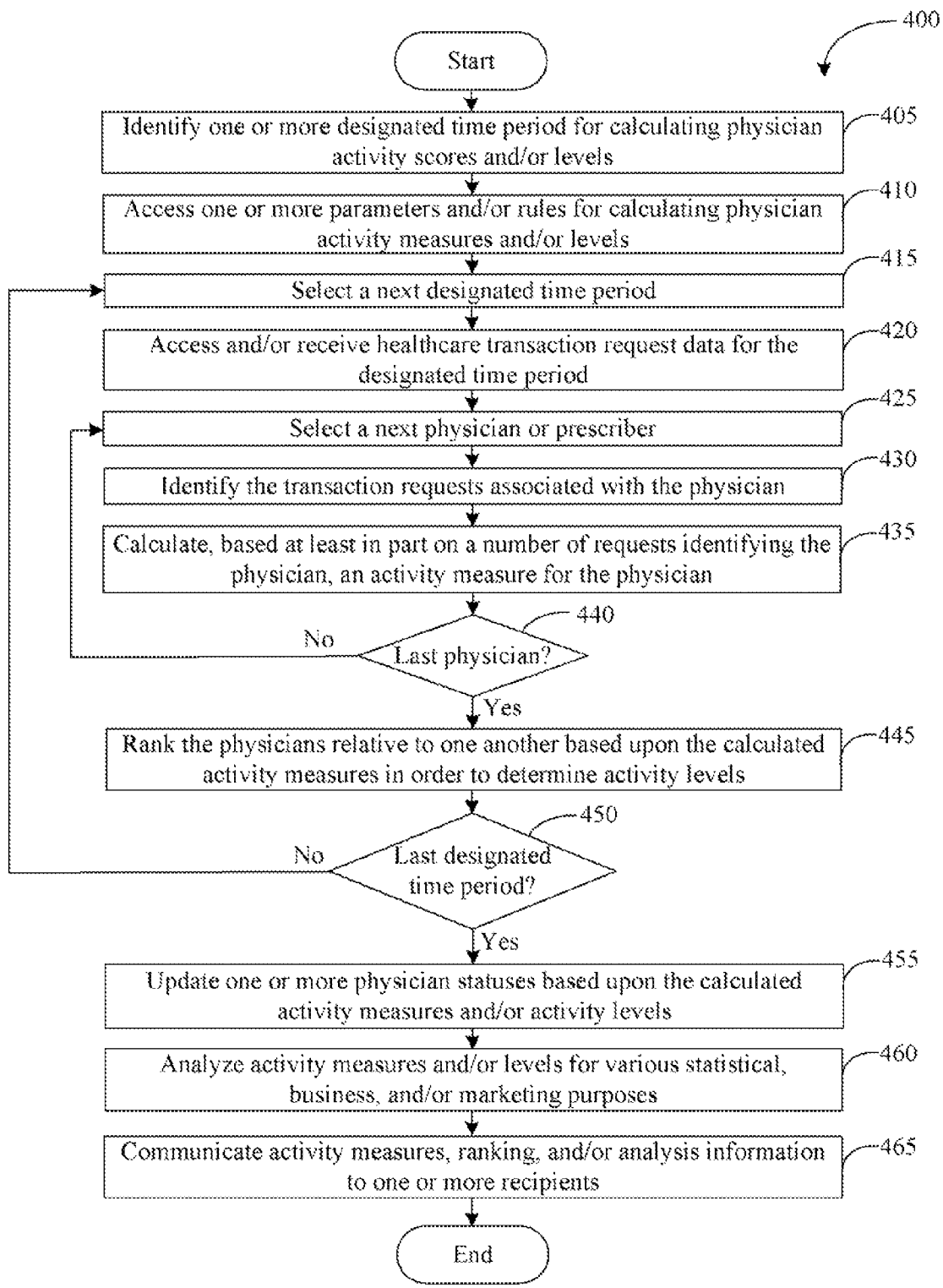
FIG. 4 is a flow chart of an example method for determining prescribing physician activity levels, according to an illustrative embodiments of the invention.

FIG. 4 is a flow chart of an example method 400 for determining prescribing physician activity levels, according to an illustrative embodiments of the invention. The method 300 may be performed by a suitable service provider computer and/or an associated physician activity level module, such as the service provider computer 106 and physician activity level module 180 illustrated in FIG. 1. In certain embodiments, the method 400 may be performed periodically, such as once a day. In other embodiments, the method 400 may be performed based upon the receipt of a request for physician activity information. The method 400 may begin at block 405.

At block 405, one or more designated time periods for calculated physician activity measures and/or physician activity levels may be identified. For example, a designated time period may be accessed from memory or received from an entity that is requesting physician activity information. A wide variety of designated time periods may be utilized as desired in various embodiments of the invention. Additionally, respective physician activity measures and/or levels may be calculated for any number of designated time periods. In one example embodiment, a relatively short term time period (e.g., a historical time period of the last seven days) and a longer term time period (e.g., a historical time period of the last ninety days) may be identified, although other designated time periods may be utilized.

At block 410, one or more parameters and/or rules for calculating or determining physician activity measures and/or levels may be accessed, received, and/or otherwise obtained. A wide variety of parameters and/or rules may be utilized as desired in various embodiments of the invention, including but not limited to, one or more formulas for calculating activity measures, one or more parameters for ranking physicians according to their activity measures, one or more parameters for determining activity levels, one or more parameters associated with particular physicians, types of physicians, and/or classifications of physicians to be analyzed and/or ranked, etc.

At block 415, a next designated time period may be selected. For example, a first designated time period identified at block 405 may be selected. At block 420, healthcare transaction request data for the selected designated time period may be accessed from memory, received from a third party data source, and/or otherwise obtained for processing. For example, if the selected designated time period is a seven day historical time period, then information associated with healthcare transaction requests that have been processed by the service provider computer 106 within the last seven days may be accessed from memory. As another example, information associated with a respective number of prescriptions associated with a plurality of doctors for the designated time period or for individuals days included in the time period may be accessed.

Each transaction request may be associated with a respective prescribing physician. As desired, the transaction request information may be sorted by prescribing physician. Alternatively, a number of transaction requests associated with a particular physician may be stored at the end of each day. The transaction request information may then be analyzed for each physician in order to calculate an activity measure for the physician during the selected time period. For example, at block 425, a next physician or prescriber may be selected. The healthcare transaction requests associated with the selected physician may be identified at block 430. A number of healthcare transaction requests for the time period that are associated with the selected physician may be identified. As desired, various information associated with the transaction requests for a physician may also be identified, such as a healthcare provider (e.g., a pharmacy) that originated a healthcare claim transaction or received an electronic prescription order that is associated with the physician, geographical information associated with the physician and/or healthcare providers, product information (e.g., therapeutic class or drug type information, etc.) for various transactions, and/or other suitable information. In certain embodiments, a number of pharmacies that processed healthcare claim requests for the physician may be identified. Additionally, duplicate transaction requests may be identified and condensed as desired in certain embodiments. For example, an electronic prescription order communicated to a pharmacy and a claim transaction that is generated by the pharmacy may be consolidated into a single healthcare claim request and/or counted as a single healthcare claim request.

At block 435, an activity measure or activity score for the physician may be calculated or determined based at least in part on a number of healthcare transaction requests that identify the physician. As desired, any number of other parameters, such as a number of pharmacies associated with the healthcare transaction requests, may also be utilized in the calculation of an activity measure for the physician. Other example parameters that may be utilized in a calculation include, but are not limited to, geographical information associated with the transactions (e.g., geographical information for the healthcare providers), product information (e.g., therapeutic class, drug classification, product identifiers, product names, etc.) associated with the transactions, etc. In fact, a wide variety of different calculations may be performed in accordance with various embodiments of the invention. In one example embodiment, an activity measure for a physician may be calculated in accordance with the formula set forth in equation 1 above.

At block 440, a determination may be made as to whether the physician is the last physician for which claims have been identified within the designated time period that is being analyzed. If it is determined at block 440 that the physician is not the last physician, then operations may continue at block 425 and a next physician may be selected for analysis. In this regard, a respective activity measure may be calculated for each physician that is identified by healthcare transaction requests associated with the designated time period. If, however, it is determined at block 440 that the physician is the last physician, then operations may continue at block 445.

At block 445, the physicians may be ranked relative to one another based upon their calculated activity measures. Respective activity levels for each of the physicians may then be determined based upon the ranking. The physicians may be ranked and/or grouped in a wide variety of different ways. For example, the physicians may be ranked in an ascending or descending manner by the calculated activity measures. The physicians may then be divided into groups in accordance with their rankings. In one example embodiment, the ranked physicians may be divided into a predetermined number of groups (e.g., ten groups) having an approximately equal group size. Activity levels may then be assigned to each group and the physicians included in that group. In another example embodiment, threshold activity measures may be utilized to assign activity levels to physicians. For example, the physicians having a measure that is greater than a first threshold may be assigned a first activity level. The physicians having a measure that is lower than the first threshold but higher than a second threshold may be assigned a second activity level, and so on until each physician has been assigned an activity level. Other methods may be utilized as desired to assign activity levels, and it will be appreciated that the procedures set forth above are provided by way of example only.

Once each of the physicians has been assigned an activity level for the designated time period at block 445, operations may continue at block 450. At block 450, a determination may be made as to whether the selected designated time period is the last designated time period. If it is determined at block 450 that the selected time period is not the last designated time period, then operations may continue at block 415 and a next designated time period may be selected. In this regard, physician activity measures and/or activity levels may be calculated or determined for multiple time periods, such as a relatively short term period and a longer term period. If, however, it is determined at block 450 that the selected timer period is the last designated time period, then operations may continue at block 455.

Calculated physician activity measures and/or relative activity levels may be utilized for a wide variety of different purposes as desired in various embodiments of the invention. For example, at block 455, which may be optional in certain embodiments of the invention, the calculated activity measures and/or activity levels may be utilized to update one or more physician statutes. For example, the status of physician having an inactive status may be updated to an active status if a determination is made that the physician is writing enough prescriptions to be assigned a requisite activity level. As another example, the status of a physician having an active status may be flagged or updated to an inactive status if a determination is made that the physician has not written any prescriptions in a relatively long time. For example, if no activity measure or activity level is determined for a physician by analyzing historical requests for ninety days or one hundred and eighty days, then a determination may be made that the physician is inactive.

At block 460, which may be optional in certain embodiments of the invention, activity measures and/or activity levels may be analyzed for a wide variety of different statistical, business, and/or marketing purposes. For example, activity measures and/or levels may be utilized to identify new physicians, to determine whether a physician is violating applicable sanctions, to detect fraud or potential fraud, to determine a relative practice size and/or geographical scope for a physician or group of physicians, to determined prescribing trends for physicians and/or groups of physicians, and/or for a wide variety of other purposes. A few examples of analysis that may be performed is described in greater detail above with reference to FIG. 1.

At block 465, which may be optional in certain embodiments of the invention, physician activity measures, rankings, activity levels, and/or various statistical and/or analytical information associated with the measures, rankings, and/or activity levels, may be communicated to one or more recipients, such as to one or more healthcare provider computers, healthcare provider back office computers (e.g., central systems for pharmacy chains), drug manufacturer back office computers, etc. The recipients may utilize the received information for a wide variety of analytical, business, and/or marketing purposes.

The method 400 may end following block 465.

The operations described and shown in the methods 300, 400 of FIGS. 3-4 may be carried out or performed in any suitable order as desired in various embodiments of the invention. Additionally, in certain embodiments, at least a portion of the operations may be carried out in parallel. Furthermore, in certain embodiments, less than or more than the operations described in FIGS. 3-4 may be performed.

Various block and/or flow diagrams of systems, methods, apparatuses, and/or computer program products according to example embodiments of the invention are described above. It will be understood that one or more blocks of the block diagrams and flow diagrams, and combinations of blocks in the block diagrams and flow diagrams, respectively, can be implemented by computer-executable program instructions. Likewise, some blocks of the block diagrams and flow diagrams may not necessarily need to be performed in the order presented, or may not necessarily need to be performed at all, according to some embodiments of the invention.

These computer-executable program instructions may be loaded onto a special purpose computer or other particular machine, a processor, or other programmable data processing apparatus to produce a particular machine, such that the instructions that execute on the computer, processor, or other programmable data processing apparatus create means for implementing one or more functions specified in the flowchart block or blocks. These computer program instructions may also be stored in a computer-readable memory that can direct a computer or other programmable data processing apparatus to function in a particular manner, such that the instructions stored in the computer-readable memory produce an article of manufacture including instruction means that implement one or more functions specified in the flow diagram block or blocks. As an example, embodiments of the invention may provide for a computer program product, comprising a computer usable medium having a computer readable program code or program instructions embodied therein, said computer readable program code adapted to be executed to implement one or more functions specified in the flow diagram block or blocks. The computer program instructions may also be loaded onto a computer or other programmable data processing apparatus to cause a series of operational elements or steps to be performed on the computer or other programmable apparatus to produce a computer-implemented process such that the instructions that execute on the computer or other programmable apparatus provide elements or steps for implementing the functions specified in the flow diagram block or blocks.

Accordingly, blocks of the block diagrams and flow diagrams support combinations of means for performing the specified functions, combinations of elements or steps for performing the specified functions and program instruction means for performing the specified functions. It will also be understood that each block of the block diagrams and flow diagrams, and combinations of blocks in the block diagrams and flow diagrams, can be implemented by special-purpose, hardware-based computer systems that perform the specified functions, elements or steps, or combinations of special purpose hardware and computer instructions.

Many modifications and other embodiments of the invention set forth herein will be apparent having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A computer-implemented method, comprising:
    collecting information associated with a plurality of healthcare transaction requests that are received during a designated time period from at least one healthcare provider computer for communication to at least one healthcare transaction processor computer;
    identifying a respective prescribing physician and a pharmacy for one or more of the plurality of received healthcare transaction requests; and
    calculating, for each identified physician and based upon a respective number of the healthcare transaction requests identifying the physician and the pharmacy, a respective activity measure based at least in part on a number of identified pharmacies for the identified physician for the designated time period, wherein calculating the respective activity measure of each identified physician comprises multiplying the number of the healthcare transaction requests identifying the physician by a value of two minus one over the number of pharmacies;

wherein the above operations are performed by one or more computers associated with a service provider.

2. The method of claim 1, further comprising:
ranking the identified physicians relative to one another based upon the calculated activity measures for the identified physicians; and
determining, based upon the ranking, a respective activity level for each identified physician.

3. The method of claim 1, wherein the identifying of the respective prescribing physician comprises identifying a physician by a subscriber identifier included in a healthcare transaction requests.

4. The method of claim 1, wherein the plurality of healthcare transaction requests comprise at least one of (i) a healthcare claim transaction or (ii) an electronic prescription request.

5. The method of claim 1, wherein the designated time period comprises a first designated time period and a second designated time period different than the first designated time period, and
wherein calculating a respective activity measure for the designated time period comprises calculating a first respective activity measure for the first designated time period and calculating a second respective activity measure for the second designated time period.

6. The method of claim 1, further comprising:
utilizing a calculated activity measure for an identified physician to facilitate one of (i) detecting whether the identified physician is a new physician, (ii) determining whether the identified physician is violating applicable sanctions, (iii) detecting fraud associated with the identified physician, (iv) determining a relative practice size for the identified physician, or (v) determining a prescribing trend associated with the identified physician.

7. The method of claim 1, further comprising:
utilizing the plurality of respective activity measures to determine that a physician that is not one of the identified physicians has become inactive.

8. The method of claim 1, further comprising:
utilizing a calculated activity measure for an identified physician to update a status associated with the identified physician.

9. A system, comprising:
at least one memory operable to store computer-executable instructions; and
at least one processor configured to access the at least one memory and execute the computer-executable instructions to:
collect information associated with a plurality of healthcare transaction requests that are received during a designated time period from at least one healthcare provider computer for communication to one or more healthcare transaction processor computers;
identify a respective prescribing physician and a pharmacy for one or more of the plurality of received healthcare transaction requests; and
calculate, for each identified physician and based upon a respective number of the healthcare transaction requests identifying the physician and the pharmacy, a respective activity measure based at least in part on a number of identified pharmacies for the identified physician for the designated time period, wherein the respective activity measure for an identified physician is calculated by multiplying the number of the healthcare transaction requests identifying the physician by a value of two minus one over the number of pharmacies.

10. The system of claim 9, wherein the at least one processor is further configured to execute the computer-executable instructions to:
rank the identified physicians relative to one another based upon the calculated activity measures for the identified physicians; and
determine, based upon the ranking, a respective activity level for each identified physician.

11. The system of claim 9, wherein a respective prescribing physician is identified by a subscriber identifier included in a healthcare transaction request.

12. The system of claim 9, wherein the plurality of healthcare transaction requests comprise at least one of (i) a healthcare claim transaction or (ii) an electronic prescription request.

13. The system of claim 9, wherein the designated time period comprises a first designated time period and a second designated time period different than the first designated time period, and
wherein the at least one processor is further configured to execute the computer-executable instructions to calculate a first respective activity measure for the first designated time period and a second respective activity measure for the second designated time period.

14. The system of claim 9, wherein the at least one processor is further configured to execute the computer-executable instructions to:
utilize a calculated activity measure for an identified physician to facilitate one of (i) detecting whether the identified physician is a new physician, (ii) determining whether the identified physician is violating applicable sanctions, (iii) detecting fraud associated with the identified physician, (iv) determining a relative practice size for the identified physician, or (v) determining a prescribing trend associated with the identified physician.

15. The system of claim 9, wherein the at least one processor is further configured to execute the computer-executable instructions to:
utilize the plurality of respective activity measures to determine that a physician that is not one of the identified physicians has become inactive.

16. The system of claim 9, wherein the at least one processor is further configured to execute the computer-executable instructions to:
utilize a calculated activity measure for an identified physician to update a status associated with the identified physician.

* * * * *